(12) United States Patent
Ryan

(10) Patent No.: US 7,205,145 B2
(45) Date of Patent: Apr. 17, 2007

(54) GAS-BORNE MATTER COLLECTION DEVICE

(75) Inventor: Scott Ryan, Ocala, FL (US)

(73) Assignee: Zefon International, Inc., Ocala, FL (US)

( * ) Notice: Subject to any disclaimer, the term of this patent is extended or adjusted under 35 U.S.C. 154(b) by 128 days.

(21) Appl. No.: 10/808,114

(22) Filed: Mar. 24, 2004

(65) Prior Publication Data

US 2005/0214745 A1 Sep. 29, 2005

(51) Int. Cl.
*C12M 1/26* (2006.01)

(52) U.S. Cl. ............... 435/309.1; 422/83; 422/102; 73/28.05; 73/863.22

(58) Field of Classification Search ............... None
See application file for complete search history.

(56) References Cited

U.S. PATENT DOCUMENTS

| | | | |
|---|---|---|---|
| 3,932,220 A | 1/1976 | Liotta | |
| 3,940,250 A | 2/1976 | Plakas et al. | |
| 4,038,057 A * | 7/1977 | Roth | 73/863.22 |
| 4,783,401 A | 11/1988 | Horan et al. | |
| 4,883,644 A | 11/1989 | Perlman | |
| 5,268,460 A | 12/1993 | Thorne et al. | |
| 5,529,914 A | 6/1996 | Hubbell et al. | |
| 5,589,154 A | 12/1996 | Anderson | |
| 5,693,895 A | 12/1997 | Baxter | |
| 5,780,295 A | 7/1998 | Livesey et al. | |
| 5,840,573 A | 11/1998 | Fields | |
| 6,406,906 B1 * | 6/2002 | Herbig et al. | 735/297.1 |
| 6,514,721 B2 * | 2/2003 | Spurrell | 435/30 |
| 6,925,853 B2 | 8/2005 | Radolovich | |
| 2002/0066321 A1 * | 6/2002 | Lagraff et al. | 73/863.22 |
| 2003/0068777 A1 * | 4/2003 | Nakano et al. | 435/69.1 |
| 2003/0207304 A1 * | 11/2003 | Black et al. | 435/6 |
| 2004/0058428 A1 * | 3/2004 | Perlman et al. | 435/252.3 |
| 2004/0185554 A1 * | 9/2004 | Daitch et al. | 435/309.1 |

* cited by examiner

*Primary Examiner*—David Redding
(74) *Attorney, Agent, or Firm*—Foley & Lardner LLP (57) ABSTRACT

A device for collecting viable gas-borne matter includes an inlet and an outlet and a plate provided intermediate the inlet and the outlet and having a first surface facing the inlet and a second surface facing the outlet. A substance is provided on the first surface of the plate for capturing viable matter carried in a gas drawn through the inlet. The substance is configured to maintain the viable matter in a living state without promoting growth of the viable matter.

53 Claims, 2 Drawing Sheets

GAS-BORNE MATTER COLLECTION DEVICE

FIELD

The present invention relates generally to the field of airborne matter collection devices. More specifically, the present invention relates to devices that enable collection and maintenance of viable matter carried in a gaseous atmosphere.

BACKGROUND

Air sampling devices are generally used to determine the quantity and types of matter present in a gas (e.g., air or other gaseous atmospheres). For example, in a factory where materials are used that may be detrimental to human health, it may be desirable to determine the amount and types of matter present in the atmosphere so that factory workers are not exposed to unsafe or undesirable levels of airborne materials. In other examples, air sampling devices may be used in a variety of environments, including, but not limited to, office buildings, houses, hospitals, clean rooms, or outdoors.

Sampling devices conventionally include a collection device (e.g., a particle impaction device, microscope slide, petri dish, or other device) for collecting and retaining matter included in the gas being sampled. In use, the sampling device draws a gas (e.g., air) toward the collection device. Matter included in the gas impacts a substance or material (e.g., a collection medium) provided on or in the collection device, where the matter is retained until analysis can be performed. One known type of collection device is a cassette or cartridge type sampling device, such as the Air-O-Cell product manufactured by the assignee of the present application, Zefon International, Inc. of Ocala, Fla.

Conventional collection devices may not be ideally suited for sampling viable matter (e.g., organisms) such as mold spores, bacteria, viruses, and other viable matter. For example, some collection devices are designed to collect non-viable matter (e.g., particulate matter, asbestos, etc.), and utilize a collection medium (e.g., a dry filter or a tacky or sticky surface) that may dehydrate or desiccate viable matter. Dehydration may damage or destroy the viable matter, which may impede or prevent subsequent analysis or examination. Another difficulty with the use of such a collection medium is that removal of the viable matter may be difficult or impossible, which may prevent transfer of the viable matter to a growth medium (e.g., an agar medium) for further development or maturation.

Other types of known collection devices are designed to collect-viable matter directly into a growth medium. For example, a collection device such as a petri dish may include an agar medium (e.g., malt extract agar, potato extract agar, etc.). In use, viable matter is impacted directly into the growth medium, where the viable matter develops or matures due to the presence of nutrients in the growth medium. The use of growth medium as an impaction material may present a variety of difficulties. For example, agar media must typically be kept cool during storage and shipping by refrigeration or similar methods. Even with refrigeration, agar media must be used within a relatively short period of time (e.g., 30 days). Accordingly, collection devices using agar media have a relatively short "shelf life" and must either be used within the life of the product or discarded.

Another difficulty with the use of growth media in collection devices relates to the fact that certain types of viable matter require specific types of agar media. For example, certain types of viable matter may require a malt extract agar, blood agar, soy agar, etc. It may therefore be necessary to obtain a number of air samples in a variety of different growth media types to ensure that the types of viable matter present in the air are collected in appropriate growth media. Removal of viable matter from one growth medium and transfer of the viable matter to a different growth medium is difficult or impossible. Collecting a number of air samples may not be practical or feasible in certain situations. For example, if an individual has a single sampling device and wishes to obtain multiple air samples during a particular time period, such sampling may be impossible given the time required to obtain a sample. Even where obtaining multiple samples is possible, such sampling is inefficient in that either multiple samples must be taken sequentially or multiple air sampling devices must be used concurrently.

Yet another difficulty with the use of conventional collection devices is that the collection devices may become contaminated with continued use. For example, after sampling is complete, the collection medium (e.g., agar medium) is removed from the collection device and the collection device is cleaned. Remnants of past samples and media may remain after cleaning, which may affect results of subsequent sampling.

Yet still another difficulty with conventional collection devices is that sampling may not achieve desired results. For example, if the amount of time for a particular sample is too long, there may be an excess of sampled matter, which will prevent growth of viable matter and counting of viable matter due to overcrowding of the sample medium. If sampling time is too short, there may be insufficient amount of sampled matter for analysis. In such a situation, the possibility of obtaining a false reading may be greatly enhanced.

Yet further still another difficulty with conventional collection devices is that the user must place an appropriate amount of collection medium on or in the collection device. Variability due to human error in the thickness and amount of collection medium may affect results of subsequent sampling. For example, overloading the collection device with collection medium may alter the gas flow characteristics of the device (e.g., the collection medium may block an air inlet) or collection efficiency may be reduced.

SUMMARY

An exemplary embodiment relates to a device for collecting viable gas-borne matter. The device includes an inlet and an outlet and a plate provided intermediate the inlet and the outlet and having a first surface facing the inlet and a second surface facing the outlet. The device also includes a substance provided on the first surface of the plate for capturing viable matter carried in a gas drawn through the inlet. The substance is configured to maintain the viable matter in a living state without promoting growth of the viable matter.

Another exemplary embodiment relates to a collection device for use in sampling gas that contains viable matter. The collection device includes a suspension medium for preserving viable matter in a living state and means for directing a flow of gas toward the suspension medium. The suspension medium is configured for capturing viable matter included in the gas as the gas is drawn through the means for directing a flow of gas Another exemplary embodiment relates to a plate for use in a gas-borne matter collection device. The plate includes a substance provided on a surface of the plate for preserving viable matter in a living state without generally promoting growth of the viable matter.

Another exemplary embodiment relates to a method of collecting viable matter included in a gaseous atmosphere. The method includes directing a flow of gas toward a suspension medium, the suspension material configured to maintain viable matter in a living state. The method also includes capturing viable matter carried in the gas in the suspension material and removing the viable matter from the suspension material.

DETAILED DESCRIPTION OF EXEMPLARY EMBODIMENTS

With reference to FIGS. 1–4, a collection device or apparatus 10 configured for use with a pump or other air sampling device (e.g., a device which forces air through the collection device that is either directly or indirectly connectable to the collection device) (not shown) is shown according to an exemplary embodiment. Collection device 10 is shown in the form of a cassette or cartridge, although various configurations for may be used according to other exemplary embodiments. One advantageous feature of the exemplary embodiment shown in FIGS. 1–4 is that the collection device allows for longer sampling times, which improves the accuracy of sampling. For example, using a suspension medium, because there is no agar to overload, allows more matter to be collected in a longer sampling period.

According to an exemplary embodiment, collection device 10 is configured for use with a sampling device that draws air or other gases through the collection device (e.g., using an impeller, blower fan, or other type of fan or pump) to collect matter contained in or carried by the air or gases. According to other exemplary embodiments, other configurations for the collection device may be used, which may or may not require the use of a sampling device.

Collection device 10 includes a top or upper portion 20, a bottom or lower portion 40, and a sampling plate or slide 50. Collection device 10 may be disassembled by decoupling top portion 20 and bottom portion 40 to allow removal of plate 50 after sampling has been completed. Top portion 20 and bottom portion 40 may be made from a variety of materials, including polymeric, metal, ceramic, glass, or other materials suitable for use in a collection device.

According to an exemplary embodiment, collection device 10 has a size and shape configured for coupling with a sampling device. For example, a rubber grommet tubing or other feature of the sampling device may couple to collection device 10 to relatively securely retain collection device 10 in place.

According to the exemplary embodiment shown in FIGS. 1–4, collection device 10 has a relatively cylindrical shape. According to other exemplary embodiments, other sizes and shapes for the collection device may be used. For example, according to another exemplary embodiment, a collection device may have a rectangular solid or cubic shape.

Figure 1:
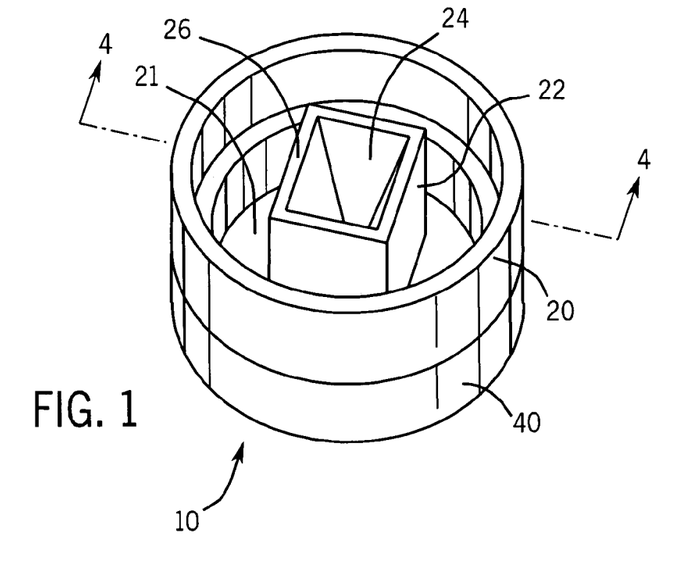
FIG. 1 is a perspective view of a collection device according to an exemplary embodiment.
Figures 2, 3:
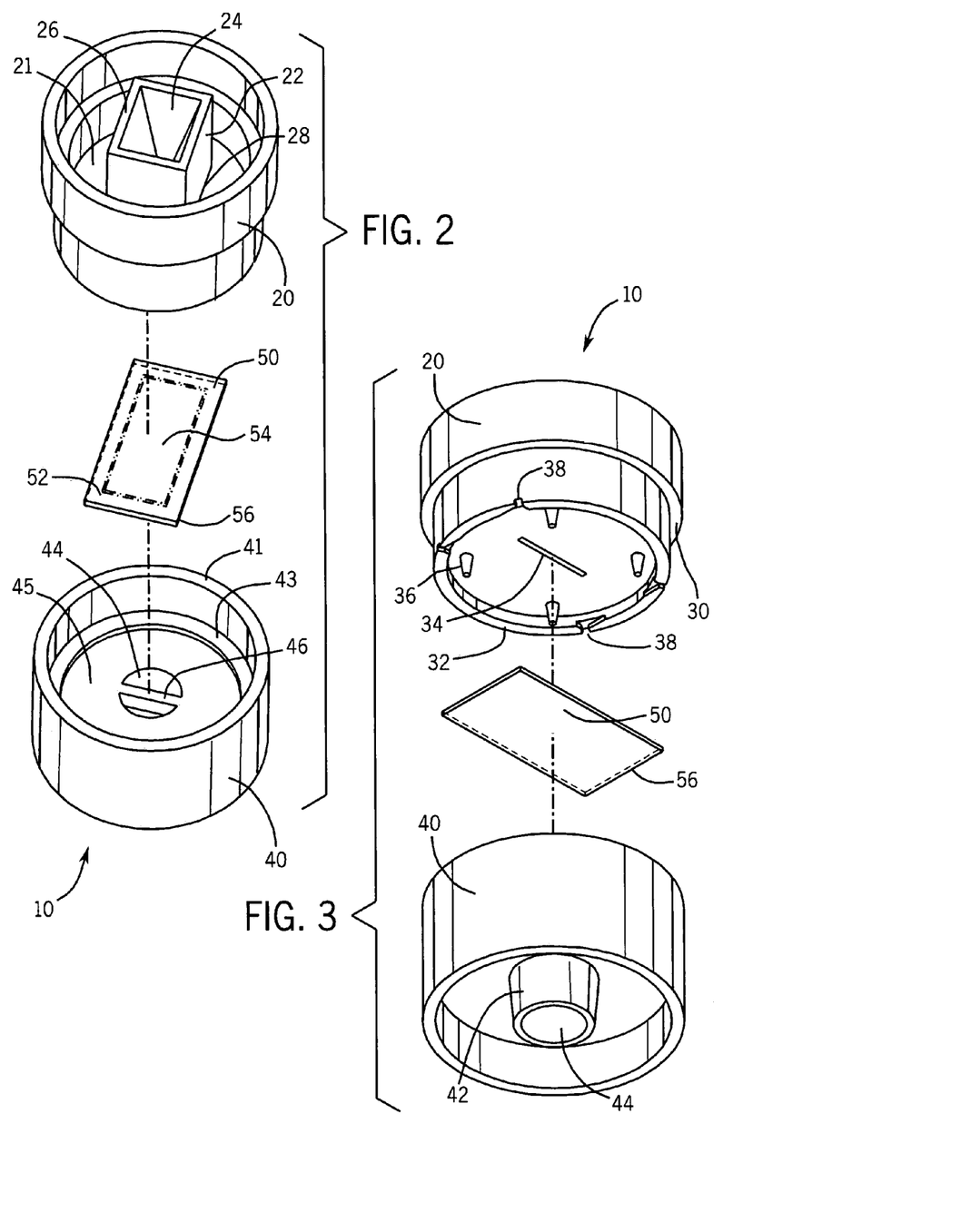
FIG. 2 is an exploded perspective top view of the collection device shown in FIG. 1.
FIG. 3 is an exploded perspective bottom view of the collection device shown in FIG. 1.
Figure 4:
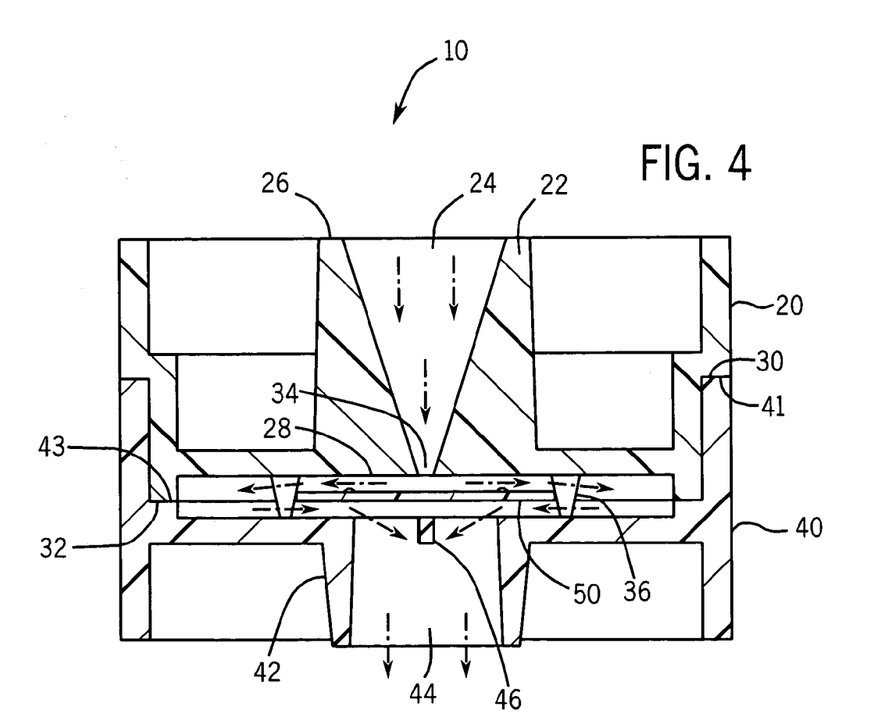
FIG. 4 is a cross-sectional view of the collection device shown in FIG. 1, the cross-sectional view being taken across line 4—4.

Top portion 20 includes an inlet 22 that defines an aperture or opening 24 through which gas is drawn during sampling. According to an exemplary embodiment, the size of aperture 24 defined by inlet 22 narrows from a top portion 26 to a bottom portion 28 of inlet 22. Aperture 24 has a generally rectangular shape when viewed in the axial direction. The size (e.g., area) of the rectangle decreases from top portion 26 to bottom portion 28 in a substantially continuous manner. According to an exemplary embodiment, the width of aperture 24 (e.g., the longer side of the rectangle) remains constant between top portion 26 and bottom portion 28 while the length (e.g., the shorter side of the rectangle) decreases with increasing distance from top portion 26. As shown in FIG. 4, a cross-sectional view of inlet 22 taken along line 4—4 in FIG. 1 shows that aperture 24 has a generally trapezoidal shape when viewed in the longitudinal direction due to the decreasing size of aperture 24 with increasing distance from top portion 26. Aperture 24 thus narrows to form a slit 34 in a surface 21 of top portion 20.

According to another exemplary embodiment, both the length and width of the rectangle forming the aperture decrease with increasing distance from the top of the inlet. According to other alternative embodiments, the shape of the inlet and/or aperture may differ. For example, an aperture may have a generally circular, square, oval, or other shape when viewed in the axial direction. Such inlets and/or apertures according to alternative embodiments may or may not decrease in area with increasing distance from the top of the inlets. For example, where an aperture and/or inlet is provided with a generally circular cross-section viewed in the axial direction, the aperture and/or inlet may resemble a funnel (e.g., the area decreases with increasing distance from the top of the inlet) or may resemble a cylinder (e.g., the area does not decrease with increasing distance from the top of the inlet). Any of a variety of shapes and configurations may be provided for the aperture and/or inlet according to various other embodiments, and the shape, size, and other characteristics may be optimized for a particular application.

Bottom portion 40 of collection device 10 includes an outlet or exit port 42 defining an aperture or opening 44 through which air is drawn during sampling. A beam or bar 46 is provided across aperture 44 and is integrally formed with a surface 45 provided in bottom portion 40. Beam 46 acts as a stop to prevent objects from being inserted through aperture 44, which might otherwise collide with and damage or destroy plate 50.

According to an exemplary embodiment, outlet 42 has a generally circular shape when viewed in the axial direction and tapers from a larger diameter to a smaller diameter with increasing distance from a surface 45 provided in bottom portion 40. According to alternative embodiments, the size and/or shape of outlet 42 may differ. For example, according to another exemplary embodiment, the outlet may have a generally square or oval shape when viewed in the axial direction. Further, the outlet may or may not taper along its length.

While collection device 10 is shown as having a single outlet and a single inlet, according to other exemplary embodiments, any number of outlets and inlets may be provided in a collection device having any of a variety of different configurations (e.g., one outlet may have a relatively circular opening while a second outlet may have a relatively rectangular opening, etc.). A sampling plate or slide may have different sampling mediums (e.g., suspension media) provided in different areas such that a different sampling medium is provided adjacent each of the plurality of inlets.

When collection device 10 is assembled, a portion of top portion 20 is inserted within bottom portion 40 such that a first rim or surface 30 provided on top portion 20 abuts a first rim or surface 41 provided on bottom portion 40 and a second rim or surface 32 provided on top portion 20 abuts a second rim or surface 43 provided on bottom portion 40. Plate 50 is provided intermediate a top portion 20 and a bottom portion 40 of collection device 10 (and hence between inlet 22 and outlet 42). A top surface 52 of plate 50 is provided adjacent or proximate slit 34 formed in bottom surface 21 of top portion 20. According to other exemplary embodiment, other ways of connecting the top portion to the bottom portion may be utilized (e.g., glue, fasteners such as screws and bolts, welding, etc.).

To secure plate 50 in relation to inlet 22 and slit 34, projections or protrusions 36 extend outward from bottom surface 21 of top portion 20. Plate 50 is positioned between projections 36 such that projections 36 prevent lateral movement of plate 50. Additionally, corners 56 of plate 50 are received within cutouts 38 included in second rim 32 of top portion 20 to further restrict movement of plate 50 and to secure plate 50 in a relatively fixed relationship to inlet 22 and slit 34. While plate 50 is shown as having a particular shape in the accompanying FIGURES, according to other exemplary embodiments, the plate or slide may have any of a variety of sizes, shapes, and/or configurations (e.g., oval, circle, hexagon, etc.), which may be chosen based on any of a variety of factors (e.g., required size of sampling area, manufacturability, cost, etc.).

Other means of securing the plate in place may be utilized according to other embodiments. For example, either projections or cutouts may be omitted from the collection device. In another example, where a plate having a different size or shape is utilized, a different number of cutouts and/or projections may be utilized. In yet another example, neither cutouts nor projections are provided, and the plate is secured in place by a different type of feature or structure. In yet another example, the plate may be glued (e.g., using an adhesive) or ultrasonically welded in place. Any feature or structure that retains the plate in place may be utilized according to various embodiments.

While the FIGURES illustrate a collection device 10 that includes a top portion 20 that is inserted into a bottom portion 40, according to another exemplary embodiment a bottom portion may be inserted into a top portion. According to another embodiment, neither of the top and bottom portions are inserted into each other, and coupling of the top portion and bottom portion is accomplished by any of a variety of other methods. According to various other embodiments, the top and bottom portions may be secured together using adhesives, ultrasonic welding or sealing, a screw-type arrangement, a snap-fit type arrangement, or any other suitable means.

Plate 50 may be made of any suitable material, including glass, porous glass fiber filters, ceramic, porous plastic, metal (e.g., aluminum, steel, etc.), or any other suitable material (e.g., a porous rigid material). According to an exemplary embodiment, plate 50 is made of glass and has a generally rectangular shape. Plate 50 is relatively thin (e.g., between approximately 0.001 and 0.125 inches), although the thickness may vary in alternative embodiments. For example, the plate may be formed to have a thickness similar to that of conventional microscope slides. Other configurations may also be used for plate 50. For example, the plate may be made of a polymeric material and/or may be formed in the shape of an octagon, triangle, square, circle, oval, or any other suitable shape (e.g., cup-shaped, dish-shaped, etc.).

According to an exemplary embodiment, collection device 10 is a disposable or non-reusable type collection device (i.e., collection device 10 is intended as a single-use type component that is discarded after use). According to other exemplary embodiments, collection device 10 may be a reusable type collection device (e.g., the plate may be cleaned and re-inserted into the collection device or the plate may be replaced with a new plate). After sampling is complete, collection device 10 is disassembled to remove plate 50 from collection device 10 so that the matter retained in substance 54 may be quantified, tested, or otherwise analyzed. One advantageous feature of using a disposable collection device is that cleaning of the plate (e.g., removal of the suspension medium (e.g., substance 54) and captured viable matter and deposition of new or fresh suspension medium) is eliminated. A related advantageous feature of using a disposable collection device is that errors in sampling due to contamination of the suspension medium and/or to variations in application of new suspension medium material to the plate may be reduced or eliminated. According to another exemplary embodiment, plates (e.g., glass slides, etc.) may be provided as separate components for use in a collection device and sold separately from the collection device.

FIG. 4 shows a cross-sectional view of collection device 10 taken in the longitudinal direction along line 4—4 in FIG. 1. Gas flow through collection device 10 is indicated generally by dashed arrows. As shown, gas is drawn into collection device 10 through inlet 22. The velocity of the air increases as it approaches bottom portion 28 of inlet 22 due to narrowing of aperture 24. The gas then travels around plate 50 and through outlet 42. At least a portion of the gas-borne matter drawn into inlet 22 is captured by a substance or material 54 (e.g., a suspension or transport medium) provided on plate 50 when the gas changes direction to travel around plate 50.

Substance 54 is provided on top surface 52 of plate 50 and is aligned with slit 34 such that matter carried in a gas impacts substance 54 when gas is drawn through inlet 22 during sampling. In this manner, gas-borne viable matter is captured by substance 54, which has a relatively soft texture or viscosity. Non-viable gas-borne matter (e.g., pollen, dust, asbestos, and other non-viable matter) may also be captured by substance 54 during sampling.

According to an exemplary embodiment, substance 54 is configured to maintain viable matter (e.g., biological organisms such as mold spores, bacteria, skin cells, anthrax, viruses, insects and insect parts, and other viable matter) in a living state. For example, substance 54 is configured to provide hydration for viable matter included therein. In this manner, viable matter is prevented from drying out and/or dying when retained within substance 54.

According to an exemplary embodiment, substance 54 is configured to maintain viable matter in a living state for at least a predetermined amount of time (e.g., between approximately 1 and 14 days). For example, mold spores captured in the substance 54 may be kept alive in substance 54 for between approximately 2–7 days before growth may appear. The specific amount of time viable matter may be kept alive may depend on a number of factors, including the type of viable matter (e.g., mold spores, viruses, bacteria), the composition of the substance, the temperature of the sample, and other factors.

Substance 54 does not promote development or maturation (e.g., growth) of viable matter captured therein according to an exemplary embodiment. For example, substance 54 does not include nutrients in an amount adequate or sufficient to encourage growth of the viable matter. In this manner, viable matter captured by substance 54 may be transported to an appropriate growth medium (e.g., an agar medium) for culturing. One advantageous feature of such an arrangement is that captured viable matter may be introduced into a growth medium in essentially the as-captured form, so that one may observe essentially all stages of development subsequent to capture.

To prevent contamination of substance 54 with nutrients or other development-promoting materials during shipping and/or storage, collection device 10 may be sealed. For example, collection device 10 may be vacuum sealed and/or may include elements that cover inlet and 22 and outlet 42 to prevent introduction of any airborne nutrients. According to an exemplary embodiment, stickers or labels are provided to cover openings 24 and 44 during shipping and storage. According to another exemplary embodiment, caps or plugs may be provided to cover openings 24 and 44. Such stickers, labels, caps, or plugs are removed before sampling to allow the flow of gas through collection device 10, and may be replaced after sampling is completed to prevent contamination of the sample. Collection device 10 may also be shipped and/or stored in a sealed (e.g., vacuum sealed) pouch or container to further prevent contamination and reduce drying of the substance that acts as a suspension medium.

According to an exemplary embodiment, the substance 54 is produced in a manner that creates a relatively smooth material with a relatively stable viscosity between approximately 30° F. and 140° F. Substance 54 may be substantially colorless, although according to certain embodiments substance 54 may not be substantially colorless. The viscosity of such a material is sufficient to prevent slide runoff, is water soluble, and has sufficient moisture to prevent drying of the material during sampling and/or storage for at least a predetermined amount of time. Another advantageous feature of such a material is that it does not degrade during a sterilization process in which the material is autoclaved or sterilized by other methods.

According to other exemplary embodiments, other types of substances may be used that may be configured to support viable matter in a living state without promoting growth. For example, a mixture including corn starch, water, oil and/or grease, and chemical elements to sustain the viable matter may be produced. Such mixture may include a viscosity which varies with ambient temperature.

According to various exemplary embodiments, substance 54 may be a gel, semi-solid material, solid material, or liquid material. According to one exemplary embodiment, substance 54 includes water in an amount between approximately 5 to 50 percent by weight, hydrocolloid in an amount between approximately 1 and 20 percent by weight, humectants in an amount between approximately 30 and 99% by weight, and nutrients in an amount between approximately 0 and 50 percent by weight. According to other exemplary embodiments, various components may be omitted (e.g., some compositions may not utilize water, for instance).

It is intended that the hydrocolloid acts to create a gel or semi-solid material, and that the humectants are used to reduce the tendency of substance 54 to dry out during sampling and/or storage. The anti-bacterial agents reduce the possibility of unwanted bacteria growth in spore samples being taken, and the distilled water is used as a mixing and hydrating agent. Various chemical elements added in the form of nutrients are intended to provide minimal nutrition to sustain sample life (e.g., viable matter) without promoting growth of such samples.

According to various exemplary embodiments, the substance or suspension medium utilizes a formula includes one or more types of hydrocolloid with a humectant and/or various nutrients. Note that humectants and nutrients are optional (e.g., a hydrocolloid could be used by itself and/or with one or the other of humectants and nutrients). The nutrients can vary depending on what needs to be captured. For example, one type of nutrient may be used for bacteria, while different nutrients may be used for mold spores, viruses, etc. If a certain type of organism needs to be excluded, an antibacterial or antifungal material or substance may be utilized in the formula.

Substance 54 may comprise any of a variety of hydrocolloid materials depending on the particular application, including but not limited to one or more of algal type hydrocolloid materials (e.g., agar, carrageenan, alginate, etc.), botanical type hydrocolloid materials (e.g., arabic, karaya, guar, locust tara, tamarind, daraya, ghatti, tragacanth, cellulose, starch, pectin, knonjac, glactomannans, xyloglucan, etc.), microbial type hydrocolloid materials (e.g., curdlan, xanthan, dextran, gellan, B-glucans, chitosan, alginates, inulin, CRC biopolymer), animal type hydrocolloid materials (e.g., gelatin, caseinate, whey, chitosan, etc.), and/or combinations of one or more of any of these or other similar materials.

Substance 54 may comprise any of a variety of humectants depending on the particular application, including but not limited to one or more of oil or other petroleum-based humectants (e.g., mineral oil, plant oil, peanut oil, soybean oil, vegetable oil, corn oil, etc.), syrups (e.g., molasses, honey, corn syrup, fruitrim, invertase, invert sugar, glycerin, polyols, Triacetin, hydrogenated glucose syrups), polydextrose nutrients, and/or combinations of one or more of any of these or other similar materials.

Substance 54 may comprise any of a variety of nutrients and/or pH buffers that come from a variety of sources, such as sugars, cell culture serums, amino acids, blood lipids, proteins, and the like. Such nutrients and/or pH buffers may include one or more of glucose, sucrose, bovine serum, glutamic acid, albumin, hemoglobin, charcoal, sodium glycerophosphate, mercaptoacetic acid, sodium chloride, potasium citrate, potasium chloride, calcium chloride, magnesium chloride, monopotassium phosphate, disodium phosphate, sodium thioglycollate, L-cysteine hydrochloric, peptone, sodium phosphate, potassium phosphate, and the like. One or more of these materials may act as both a pH buffer and as a nutrient in certain applications.

Various anti-bacterial materials may also be utilized in substance 54 according to various exemplary embodiments, including propylene glycol, chloramphenicol, and vancomycin, for example. An antifingal such as amphotericin B may also be utilized where desired. According to other exemplary embodiments, any of a variety of other commercially available anti-bacterial materials and/or antifungals may be utilized, and the listing of particular anti-bacterial and antifungal materials is not intended to be limiting.

According to an exemplary embodiment, substance 54 is made-by first mixing chemical elements for organism survival, humectants, anti-bacterial agents, and distilled water until blended. Hydrocolloid is then added while heat is applied to the mixture at a relatively slow mixing speed to prevent the formation of bubbles or lumps. Subsequent heating of the mixture may also be utilized to reduce the viscosity.

The following are nonexclusive examples of several possible compositions that may be used for a substance 54 (e.g., a suspension medium) according to various exemplary embodiment.

EXAMPLE 1

According to this example, a substance such as substance 54 was made having a composition of approximately 20 weight percent starch and approximately 80 weight percent mineral oil. This substance is intended for use in sampling gas-borne (e.g., airborne) mold spores.

The substance was provided on slides and loaded into a housing. An inoculation solution was made having a mold concentration of 30 colony forming units (cfu) per 0.01 milliliters, and the slides were inoculated with the inoculation solution. Starting on day 0 (zero) and every 24 hours thereafter, one of the slides was prepared with 0.5 milliliters water and plated, after which the plate was incubated. After incubation, the number of colonies were counted on each of the plates. Table 1 shows the results obtained.

TABLE 1

| Day | Recovery (cfu) |
|---|---|
| 0 | 34 |
| 1 | 29 |
| 2 | 24 |
| 3 | 28 |

EXAMPLE 2

According to this example, a substance such as substance 54 was made having a composition of approximately 20 weight percent starch and approximately 80 weight percent water. This substance is intended for use in sampling gas-borne (e.g., airborne) mold spores.

The substance was provided on slides and loaded into a housing. An inoculation solution was made having a mold concentration of 28 cfu per 0.01 milliliters, and the slides were inoculated with the inoculation solution. Starting on day 0 (zero) and every 24 hours thereafter, one of the slides was prepared with 0.5 milliliters water and plated, after which the plate was incubated. After incubation, the number of colonies were counted on each of the plates. Table 2 shows the results obtained.

TABLE 2

| Day | Recovery (cfu) |
|---|---|
| 0 | 26 |
| 1 | 24 |
| 2 | 29 |
| 3 | 34 |

EXAMPLE 3

According to this example, a substance such as substance 54 was made having a composition of approximately 15 weight percent starch, approximately 55 weight percent glycerin, and approximately 30 weight percent water. This substance is intended for use in sampling gas-borne (e.g., airborne) mold spores.

The substance was provided on slides and loaded into a housing. An inoculation solution was made having a mold concentration of 28 cfu per 0.01 milliliters, and the slides were inoculated with the inoculation solution. Starting on day 0 (zero) and every 24 hours thereafter, one of the slides was prepared with 0.5 milliliters water and plated, after which the plate was incubated. After incubation, the number of colonies were counted on each of the plates. Table 3 shows the results obtained.

TABLE 3

| Day | Recovery (cfu) |
|---|---|
| 0 | 31 |
| 1 | 24 |
| 2 | 27 |
| 3 | 25 |

EXAMPLE 4

According to this example, a substance such as substance 54 was made having a composition of approximately 8 weight percent carrageenan, approximately 77 weight percent glycerin, and approximately 15 weight percent water. This substances is intended for use in sampling gas-borne (e.g., airborne) mold spores.

The substance was provided on slides and loaded into a housing. An inoculation solution was made having a mold concentration of 22 cfu per 0.01 milliliters, and the slides were inoculated with the inoculation solution. Starting on day 0 (zero) and every 24 hours thereafter, one of the slides was prepared with 0.5 milliliters water and plated, after which the plate was incubated. After incubation, the number of colonies were counted on each of the plates. Table 4 shows the results obtained.

TABLE 4

| Day | Recovery (cfu) |
|---|---|
| 0 | 30 |
| 1 | 19 |
| 2 | 25 |
| 3 | 23 |

EXAMPLE 5

According to this example, a substance such as substance 54 was made having a composition of approximately 4 weight percent gellan, approximately 1 weight percent calcium chloride, approximately 75 weight percent polyols, and approximately 20 weight percent water. This substance is intended for use in sampling gas-borne (e.g., airborne) mold spores.

The substance was provided on slides and loaded into a housing. An inoculation solution having mold was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in mold testing applications.

EXAMPLE 6

According to this example, a substance such as substance 54 was made having a composition of approximately 12 weight percent pectin, approximately 74 weight percent polyols, and approximately 14 weight percent water. This substance is intended for use in sampling gas-borne (e.g., airborne) mold spores.

The substance was provided on slides and loaded into a housing. An inoculation solution having mold was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in mold testing applications.

EXAMPLE 7

According to this example, a substance such as substance 54 was made having a composition of approximately 3 weight percent gellan, approximately 1 weight percent calcium chloride, approximately 76 weight percent glycerin, and approximately 20 weight percent water. This substance is intended for use in sampling gas-borne (e.g., airborne) mold spores.

The substance was provided on slides and loaded into a housing. An inoculation solution was made having a mold concentration of 28 cfu per 0.01 milliliters, and the slides were inoculated with the inoculation solution. Starting on day 0 (zero) and every 24 hours thereafter, one of the slides was prepared with 0.5 milliliters water and plated, after which the plate was incubated. After incubation, the number of colonies were counted on each of the plates. Table 5 shows the results obtained.

TABLE 5

| Day | Recovery (cfu) |
|---|---|
| 0 | 28 |
| 1 | 24 |
| 2 | 30 |
| 3 | 33 |

EXAMPLE 8

According to this example, a substance such as substance 54 was made having a composition of approximately 8 weight percent carrageenan, approximately 52 weight percent water, and approximately 40 weight percent honey. This substance is intended for use in sampling gas-borne (e.g., airborne) mold spores.

The substance was provided on slides and loaded into a housing. An inoculation solution having mold was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in mold testing applications.

EXAMPLE 9

According to this example, a substance such as substance 54 was made having a composition of approximately 8 weight percent carrageenan, approximately 35 weight percent water, and approximately 57 weight percent corn syrup. This substance is intended for use in sampling gas-borne (e.g., airborne) mold spores.

The substance was provided on slides and loaded into a housing. An inoculation solution having mold was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in mold testing applications.

EXAMPLE 10

According to this example, a substance such as substance 54 was made having a composition of approximately 18 weight percent gelatin and approximately 82 weight percent water. This substance is intended for use in sampling gas-borne (e.g., airborne) mold spores.

The substance was provided on slides and loaded into a housing. An inoculation solution was made having a mold concentration of 22 cfu per 0.01 milliliters, and the slides were inoculated with the inoculation solution. Starting on day 0 (zero) and every 24 hours thereafter, one of the slides was prepared with 0.5 milliliters water and plated, after which the plate was incubated. After incubation, the number of colonies were counted on each of the plates. Table 6 shows the results obtained.

TABLE 6

| Day | Recovery (cfu) |
|---|---|
| 0 | 26 |
| 1 | 24 |
| 2 | 29 |
| 3 | 34 |

EXAMPLE 11

According to this example, a substance such as substance 54 was made having a composition of approximately 6 weight percent galatin, approximately 79 weight percent water and approximately 15 weight percent glycerin. This substance is intended for use in sampling gas-borne (e.g., airborne) mold spores.

The substance was provided on slides and loaded into a housing. An inoculation solution was made having a mold concentration of 22 cfu per 0.01 milliliters, and the slides were inoculated with the inoculation solution. Starting on day 0 (zero) and every 24 hours thereafter, one of the slides was prepared with 0.5 milliliters water and plated, after which the plate was incubated. After incubation, the number of colonies were counted on each of the plates. Table 7 shows the results obtained.

TABLE 7

| Day | Recovery (cfu) |
|---|---|
| 0 | 18 |
| 1 | 19 |
| 2 | 25 |
| 3 | 30 |

EXAMPLE 12

According to this example, a substance such as substance 54 was made having a composition comprising mineral oil viscous. This substance is intended for use in sampling gas-borne (e.g., airborne) mold spores.

The substance was provided on slides and loaded into a housing. An inoculation solution was made having a mold concentration of 30 cfu per 0.01 milliliters, and the slides were inoculated with the inoculation solution. Starting on day 0 (zero) and every 24 hours thereafter, one of the slides was prepared with 0.5 milliliters water and plated, after which the plate was incubated. After incubation, the number of colonies were counted on each of the plates. Table 8 shows the results obtained.

TABLE 8

| Day | Recovery (cfu) |
|---|---|
| 0 | 28 |
| 1 | 20 |
| 2 | 18 |
| 3 | 22 |

EXAMPLE 13

According to this example, a substance such as substance 54 was made having a composition of 4 grams carrageenan, 3 grams sodium chloride, 1.15 grams disodium phosphate, 1 gram sodium thioglycollate, 0.2 grams potassium chloride, 0.1 grams calcium chloride, 0.1 grams magnessium chloride, 0.2 grams monopotassium phosphate, 1.0 liter glycerine, and 1.0 liter water. This substance is intended for use in sampling gas-borne (e.g., airborne) bacteria.

The substance was provided on slides and loaded into a housing. An inoculation solution having bacteria was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in bacteria testing applications.

EXAMPLE 14

According to this example, a substance such as substance 54 was made having a composition of 10 grams sodium glycerophosphate, 5 grams carrageenan, 0.5 grams L-cysteine hydrochloric, 0.5 grams sodium thioglycollate, 0.1 grams calcium chloride, 1.0 gram mercaptoacetic acid, 1.0 liter glycerine, and 1.0 liter water. This substance is intended for use in sampling gas-borne (e.g., airborne) bacteria.

The substance was provided on slides and loaded into a housing. An inoculation solution having bacteria was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in bacteria testing applications.

EXAMPLE 15

According to this example, a substance such as substance 54 was made having a composition of 5 grams carrageenan, 5 grams sodium chloride, 1.1 grams disodium phosphate, 0.1 grams calcium chloride, 1.0 liter water, and 1.0 liter glycerine. This substance is intended for use in sampling gas-borne (e.g., airborne) bacteria.

The substance was provided on slides and loaded into a housing. An inoculation solution having bacteria was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in bacteria testing applications.

EXAMPLE 16

According to this example, a substance such as substance 54 was made having a composition of 5 grams carrageenan, 5 grams sodium chloride, 1.5 grams sodium thioglycollate, 0.5 grams L-cysteine hydrochloric, 0.1 grams calcium chloride, 0.1 grams disodium Phosphate, 0.1 grams Sodium bisulfate, and 1.0 liter water. This substance is intended for use in sampling gas-borne (e.g., airborne) bacteria.

The substance was provided on slides and loaded into a housing. An inoculation solution having bacteria was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in bacteria testing applications.

EXAMPLE 17

According to this example, a substance such as substance 54 was made having a composition of 4 grams gelatin, 5 grams sodium chloride, 5 grams sodium citrate, 4 grams ammonium monohydrogenphosphate, 2 grams mono potassium phosphate, 0.5 grams sodium deoxycholate, 0.4 grams magnesium sulfate, 0.3 liters glycerin, and 0.3 liters water. This substance is intended for use in sampling gas-borne (e.g., airborne) bacteria.

The substance was provided on slides and loaded into a housing. An inoculation solution having bacteria was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in bacteria testing applications.

EXAMPLE 18

According to this example, a substance such as substance 54 was made having a composition of 4 grams gelatin, 10 grams sodium glycerophosphate, 1 gram sodium thioglycollate, 0.1 grams calcium chloride, 1.0 liter glycerin, and 1.0 liter water. This substance is intended for use in sampling gas-borne (e.g., airborne) bacteria.

The substance was provided on slides and loaded into a housing. An inoculation solution having bacteria was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in bacteria testing applications.

EXAMPLE 19

According to this example, a substance such as substance 54 was made having a composition of 75 grams sucrose, 0.52 grams dipotassium phosphate, 1.22 grams disodium phosphate, 0.72 grams glutamic acid, 50 milliliters bovine serum, 1 liter glycerine, and 1 liter water. This substance is intended for use in sampling gas-borne (e.g., airborne) bacteria.

The substance was provided on slides and loaded into a housing. An inoculation solution having bacteria was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in bacteria testing applications.

EXAMPLE 20

According to this example, a substance such as substance 54 was made having a composition of 15 grams peptone, 20 grams carrageenan, 5 grams sodium chloride, 4 grams dipotassium phosphate, 1 gram starch, 1 gram monopotassium phosphate, 250 milliliters hemoglobin, 10 milliliters vitox supplement, 730 milliliters water, and 730 milliliters glycerine. This substance is intended for use in sampling gas-borne (e.g., airborne) bacteria.

The substance was provided on slides and loaded into a housing. An inoculation solution having bacteria was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in bacteria testing applications.

EXAMPLE 21

According to this example, a substance such as substance 54 was made having a composition of 15 grams peptone, 20 grams carrageenan, 5 grams sodium chloride, 4 grams dipotassium phosphate, 1.5 grams glucose, 1 gram starch, 1 gram monopotassium phosphate, 730 milliliters water, and 730 milliliters glycerine. This substance is intended for use in sampling gas-borne (e.g., airborne) bacteria.

The substance was provided on slides and loaded into a housing. An inoculation solution having bacteria was made without controlling the concentration thereof. The slides were then inoculated with the inoculation solution. After three (3) days, the slides were prepared and plated, after which the plates were incubated and checked to ensure colony growth. It is believed that optimization of the amounts of constituents of the substance will result in a suspension medium usable in bacteria testing applications.

EXAMPLE 22

According to this example, a substance such as substance 54 may be made having a composition of 0.5 grams bovine serum, 500 grams veal infusion, 5 grams sodium chloride, 5 grams pancreatic digest of casein, 5 grams of peptic digest of animal tissue, 2 milliliters of amphotericin, 1 millileter of gentamicin, 0.2 millileters of vancomycin, and 750 milliliters of water. This substance is intended for use in sampling gas-borne (e.g., airborne) viruses. It should be noted that at the time of filing this patent application, this composition has not yet been produced or tested for use in the sampling of airborne viruses.

Substance 54 has a relatively long shelf life as compared to other conventional collection media. For example, agar media must be refrigerated during shipping and storage and has a shelf life of approximately 30 days, after which the agar media must be discarded. According to an exemplary embodiment, substance 54 does not require refrigeration during shipping and/or storage and has a shelf life of at least between approximately 1 month and 5 years. According to another exemplary embodiment, substance 54 has a shelf life of between approximately 12 and 24 months. One advantageous feature of using substance 54 is that it tends to resist drying out and cracking that may present difficulties with conventional collection media.

When sampling is completed, collection device 10 is disassembled to remove plate 50 (and hence the suspension medium and captured viable matter). Plate 50 may be removed from collection device 10 immediately after sampling is complete, or may remain in the collection device during shipping of the collection device to a remote location (e.g., a lab) or during storage. It may be desirable to seal the collection device until it is desired to remove the plate from the collection device (e.g., by re-attaching a label, sticker, plug, or cap over apertures 24 and 44 to prevent contamination of substance 54 and viable matter captured therein).

To remove viable matter from substance 54, a liquid (e.g., water, peptone solution, etc.) is utilized. According to an exemplary embodiment, substance 54 is removed from plate 50 (e.g., by scraping) and placed in a liquid to separate the substance 54 from the viable matter. According to another exemplary embodiment, the entire plate 50, including substance 54, is placed in a liquid to remove substance 54 from plate 50 and the viable matter from substance 54. In either of these embodiments, the container holding the liquid may be vibrated or shaken (e.g., using a vortexer or other device, by hand, etc.) to hasten separation of viable matter from substance 54. Further, in another exemplary embodiment, the plate may remain in the collection device and shaken or vibrated to remove viable matter. According to still another exemplary embodiment, no vibration or shaking may be used, and the substance 54 will dissolve in water or another liquid, after which the water may be sampled.

One advantageous feature of providing a substance that allows for relatively simple removal of viable matter therefrom is that the viable matter may be cultured in a variety of growth media.(e.g., agar media). For example, after removal of the viable matter from the substance as described above, a portion of the liquid (including the viable matter) may be introduced to a first type of growth media and a second portion of the liquid may be introduced to a second type of growth media. The sample may also be further diluted so that several different types of growth media may be utilized. In this manner, the necessity to perform multiple sampling operations using a variety of growth media is eliminated. According to another exemplary embodiment, all or a portion of the water or other liquid may be frozen (e.g., by freezing the entire cassette or by removing all or a portion of the liquid and freezing it). In this manner, all or a portion of the sampled liquid may be archived for later analysis.

It may be desirable to include a cyclone-type device to remove materials from the gas that exhibit a particular characteristic (e.g., particle size). For example, a cyclone-type device may be coupled to inlet 22 of collection device 10 such that gas drawn into collection device 10 first passes through the cyclone device. The cyclone device may act to remove any particles carried in the gas that have a particular size (e.g., greater or equal to approximately 2 microns).

According to other exemplary embodiments, other types and sizes of gas-borne materials may be removed from the gas prior to passage through the collection device. According to an exemplary embodiment, size selective sampling may be accomplished by providing multiple in-line cyclone devices or impaction devices so that particles or viable matter may be trapped at successive stages, with each of the stages representing a different size of sampled matter. According to another exemplary embodiment, a pre-filter or screen may be used to remove relatively large particles before impaction on substance 54 (e.g., a filter may be utilized in front of the device to remove larger particles when sampling for certain matter such as bacteria and viruses). According to yet another exemplary embodiment, multiple inlets may be provided in the collection device and used at the same time (e.g., multiple inlets are provided to allow sampling onto a single substance (e.g., substance 54) at different locations).

Collection device 10 may be utilized in a variety of different manners according to various exemplary embodiments. For example, in a first exemplary embodiment, collection device 10 may include a plate similar to plate 50 described above. The plate may be a clean substrate made of glass or another suitable material. Air sampling may be performed in such a manner that particles or other matter carried in the air are impacted directly onto the clean plate (i.e., the plate has no suspension material or other substance provided thereon). After sampling is completed, the plate may be directly sampled to an agar or other growth medium for culturing.

According to another exemplary embodiment, collection device 10 may include a plate similar to plate 50 described above, which may either be clean or may have a substance such as substance 54 or another substance provided thereon for capturing airborne matter. Airborne matter sampled onto the plate may then be suspended by adding a liquid such as water or peptone water to the collection device and retaining it therein (e.g., by plugging the inlet and outlet, etc.). Subsequent to sampling and suspension, the collection device may be drained and the liquid may be utilized with any of a variety of growth mediums for a variety of different tests (e.g., agar culturing, ELISA testing, PCR testing, etc.).

Various modifications may be made to collection device 10 that may allow for optimization for a particular use. For example, while the size of the opening at the bottom portion 28 of inlet 22 may be changed depending on the size and/or type of materials being sampled. In applications in which mold spores will be sampled, for example, the opening may have a length of approximately 0.6 inches and a width of approximately 0.030 inches. For a collection device that will be used in the collection of nanoparticles, the width of the bottom portion 28 of inlet 22 may be between approximately 0.001 and 0.005 inches. Virus sampling may utilize a width of the bottom portion 28 of inlet 22 may be between approximately 0.005 and 0.020 inches. Bacteria sampling may utilize a width of the bottom portion 28 of inlet 22 may be between approximately 0.015 and 0.025 inches. According to other exemplary embodiments, the size of the bottom portion of the opening may be optimized for the particular use and may have a different shape and/or size.

As those of skill in the art will appreciate, various advantages may be obtained using a collection device and/or suspension medium as described herein. For example, it is intended that because the collection device may be provided in a single-use form, there is no need to reload the collection device with a slide having new media provided thereon. It is also intended that the need to clean the slide or plate between uses is also eliminated. Further, it is intended that the risk of cross-contamination is reduced since the collection device is packaged in a relatively sterile environment and the slides or plates are not re-used. Contamination from the open environment may also be reduced, since the collection device may be sealed prior to shipping to the end user.

Other advantages may also be obtained. The collection device may be provided such that it is relatively compact and lightweight, which may allow it to be used in relatively tight or confined spaces. The configuration of the collection device may allow the device to be used with relatively low backpressure as compared to other devices which may require relatively large vacuum pumps to pull air through them.

The sampling medium (e.g., suspension medium) may be provided such that it need not be refrigerated, which may allow for simpler transport and storage. It is also intended that the sampling medium will have a relatively long shelf life as compared to other sampling media, and that it may be utilized to suspend the sample in a liquid or to archive the suspended solution. Further, it is intended that the sampling medium may act to eliminate or reduce the occurrence of dessication and destruction of organisms or other viable matter.

The construction and arrangement of the elements of the collection device as shown in the preferred and other exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, orientations, etc.) without materially departing from the novel teachings and advantages of the subject matter recited herein. For example, elements shown as integrally formed may be constructed of multiple parts or elements, the position of elements may be reversed or otherwise varied, and the nature or number of discrete elements or positions may be altered or varied. It should be noted that the elements and/or assemblies of the system may be constructed from any of a wide variety of materials that provide sufficient strength or durability, including any of a wide variety of moldable plastic materials in any of a wide variety of colors, textures and combinations. The order or sequence of any process or method steps may be varied or re-sequenced according to alternative embodiments. Other substitutions, modifications, changes and omissions may be made in the design, operating conditions and arrangement of the preferred and other exemplary embodiments without departing from the scope of the present invention.

What is claimed is:

1. A device for collecting viable gas-borne matter comprising:

an inlet;

an outlet;

a plate provided intermediate the inlet and the outlet and having a first surface facing the inlet and a second surface facing the outlet; and a substance provided on the first surface of the plate for capturing viable matter carried in a gas drawn through the inlet;

wherein the substance is configured to maintain the viable matter in a living state without promoting growth of the viable matter and comprises a hydrocolloid and at least one nutrient.

2. The device of claim 1, wherein the substance is at least one of a gel and a semi-solid material.

3. The device of claim 2, wherein the substance is relatively colorless.

4. The device of claim 1, wherein the hydrocolloid comprises at least one of agar, carrageenan, and alginate.

5. The device of claim 1, wherein the hydrocolloid comprises at least one of arabic, karaya, guar, locust tara, tamarind, daraya, ghatti, tragacanth, cellulose, starch, pectin, knonjac, glactomannans, xyloglucan, and combinations thereof.

6. The device of claim 1, wherein the hydrocolloid comprises at least one of curdlan, dextran, gellan, B-glucans, chitosan, alginates, inulin, and combinations thereof.

7. The device of claim 1, wherein the hydrocolloid comprises at least one of gelatin, caseinate, whey, and chitosan.

8. The device of claim 1, wherein the nutrient is one of a sugar, a cell culture serum, an amino acid, and a blood lipid.

9. The device of claim 8, wherein the nutrient is selected from the group consisting of glucose, sucrose, bovine serum, glutamic acid, albumin, hemoglobin, charcoal, sodium glycerophosphate, mercaptoacetic acid, sodium chloride, potassium citrate, potassium chloride, calcium chloride, magnesium chloride, monopotassium phosphate, disodium phosphate, sodium thioglycollate, L-cysteine hydrochloric, peptone, sodium phosphate, potassium phosphate, and combinations thereof.

10. The device of claim 1, wherein the nutrient also acts as a pH buffer.

11. The device of claim 1, wherein the substance further comprises at least one of a humectant, water, and an anti-bacterial agent.

12. The device of claim 11, wherein the humectant is selected from the group consisting of mineral oil, plant oil, peanut oil, soybean oil, vegetable oil, corn oil, molasses, honey, corn syrup, fruitrim, invertase, invert sugar, glycerin, Triacetin, an hydrogenated glucose syrup, a polydextrose nutrient, and combinations thereof.

13. The device of claim 11, wherein the anti-bacterial agent is selected from propylene glycol, vancomycin, and combinations thereof.

14. The device of claim 11, wherein the substance further comprises an antifungal.

15. The device of claim 1, wherein the substance may be stored without refrigeration between approximately 12 to 24 months.

16. The device of claim 1, wherein the substance is configured to allow removal of the viable matter from the substance in a liquid.

17. The device of claim 16, wherein the liquid is water.

18. The device of claim 1, wherein the viable matter comprises at least one of insects, insect parts, and skin cells.

19. The device of claim 1, wherein the viable matter comprises a virus.

20. The device of claim 1, wherein the viable matter comprises bacteria.

21. The device of claim 1, wherein the inlet is configured for coupling to a device configured to remove matter from the gas before the gas enters the inlet.

22. The device of claim 1, wherein the device is configured for coupling to an exterior surface of a sampling device.

23. The device of claim 1, wherein the device comprises a top portion including the inlet and a bottom portion including the outlet, wherein the device is adapted to allow decoupling of the top portion and the bottom portion to remove the plate.

24. The device of claim 1, wherein the device is a single-use product that is discarded after capturing viable matter.

25. The device of claim 1, wherein the device includes a second inlet, wherein the inlets are provided at different locations in relation to the suspension medium.

26. The device of claim 1, wherein the plate is made of at least one of glass, porous glass fibers, a ceramic material, a porous polymeric material, and a metal.

27. The device of claim 1, wherein the hydrocolloid comprises at least one of curdlan, xanthan, dextran, gellan, B-glucans, chitosan, alginates and inulin.

28. The device of claim 1, wherein the nutrient is a protein.

29. The device of claim 11, wherein the humectant is a polyol.

30. The device of claim 13, wherein the anti-bacterial agent is chloramphenicol.

31. The device of claim 1, wherein the viable matter comprises mold spores.

32. A collection device for use in sampling gas that contains viable matter comprising:

a suspension medium for preserving viable matter in a living state without promoting growth of the viable matter; and means for directing a flow of gas toward the suspension medium;

wherein the suspension medium is configured for capturing viable matter included in the gas as the gas is drawn through the means for directing a flow of gas and comprises a hydrocolloid and at least one nutrient.

33. The collection device of claim 32, wherein the means for directing a flow of gas comprises an inlet.

34. The collection device of claim 33, wherein the inlet tapers from a top of the inlet to a bottom of the inlet.

35. The collection device of claim 34, wherein the bottom of the inlet has a rectangular shape when viewed in the axial direction.

36. The collection device of claim 32, wherein the suspension medium is a gel or a semisolid material.

37. The collection device of claim 32, wherein the suspension medium is configured to preserve the viable matter without promoting further maturation of the viable matter.

38. The collection device of claim 32, wherein the suspension medium includes a humectant, an anti-bacterial agent, and a hydrocolloid.

39. The collection device of claim 32, wherein the suspension medium comprises water and at least one of mineral oil, glycerin, galatin, and carageenan.

40. The collection device of claim 32, wherein the suspension medium comprises water and at least one of gellan, glycerin, calcium chloride, a polyol, honey, corn syrup, and pectin.

41. The collection device of claim 32, wherein the viable matter comprises at least one of a bacterium and a virus.

42. The collection device of claim 32, wherein the viable matter comprises at least one of a anthrax, an insect, an insect part.

43. The collection device of claim 32, wherein the collection device is a cassette having a top portion and a bottom portion and a plate provided within the cassette, wherein the top portion and bottom portion may be separated to remove the plate.

44. The collection device of claim 32, wherein the suspension medium comprises water and starch.

45. The collection device of claim 32, wherein the viable matter comprises a mold spore.

46. A collection device for gas-borne viable matter comprising:

a plate;

a substance provided on the plate and comprising a hydrocolloid material and at least one nutrient for capturing viable matter and maintaining the viable matter in a living state without promoting growth; and an inlet for directing a gas including the viable matter toward the substance.

47. The collection device of claim 46, wherein the hydrocolloid material includes at least one material selected from the group consisting of curdlan, xanthan, dextran, gellan, B-glucans, chitosan, alginates and inulin.

48. The collection device of claim 46, wherein the substance further comprises a humectant.

49. The collection device of claim 48, wherein the humectant is a polyol and the nutrient is a protein.

50. The collection device of claim 46, wherein the substance further comprises an anti-bacterial agent comprising chloramphenicol.

51. The collection device of claim 46, wherein the substance is a gel.

52. The collection device of claim 46, wherein the collection device is configured for coupling to a sampling device.

53. The collection device of claim 46, wherein the collection device comprises a top portion comprising an inlet and a bottom portion removably coupled to the top portion.

* * * * *